United States Patent [19]

Miyazawa et al.

[11] Patent Number: 4,667,054

[45] Date of Patent: May 19, 1987

[54] PROCESS FOR PRODUCING OPTICALLY ACTIVE VALINE

[75] Inventors: Yoshinobu Miyazawa, Tokyo; Noriko Ooishi, Urawa; Shigeru Aoki, Matsudo; Yasuhisa Tashiro, Yokohama, all of Japan

[73] Assignee: Nippon Kayaku Kabushiki Kaisha, Tokyo, Japan

[21] Appl. No.: 824,089

[22] Filed: Jan. 30, 1986

[30] Foreign Application Priority Data

Feb. 13, 1985 [JP] Japan .................................. 60-24353

[51] Int. Cl.$^4$ ............................................. C07B 57/00
[52] U.S. Cl. .................................. 562/401; 562/402; 562/575
[58] Field of Search ............................... 562/401, 402

[56] References Cited

U.S. PATENT DOCUMENTS

| | | | |
|---|---|---|---|
| 2,898,358 | 8/1959 | Dowling | 562/402 X |
| 2,929,842 | 3/1960 | Fike | 562/402 |
| 3,182,079 | 5/1965 | Tatsumi et al. | 562/402 |
| 4,306,077 | 12/1981 | Leigh | 562/401 |
| 4,376,213 | 3/1983 | Nohira et al. | 562/401 |

*Primary Examiner*—Natalie Trousof
*Assistant Examiner*—Vera C. Clarke
*Attorney, Agent, or Firm*—Henry C. Nields

[57] ABSTRACT

This invention relates to a process for producing optically active valine, characterized by optically resolving DL-valine hydrochloride in a solvent containing an amine salt, a sulfonic acid or a carboxylic acid and isolating optically active valine after the decomposition of the obtained optically active valine hydrochloride.

9 Claims, No Drawings

PROCESS FOR PRODUCING OPTICALLY ACTIVE VALINE

FIELD OF THE INVENTION

This invention relates to a novel process for producing optically active valine, which is useful as a food additive, a component of an amino acid transfusion, and a raw material for agrochemicals.

BACKGROUND OF THE INVENTION

A process for producing optically active valine by the optical resolution of DL-valine hydrochloride according to preferential crystallization in solvent is already known (C.A. Vol. 59, 11659D).

When the inventors of the present invention made a follow-up of the above process, it was found the degree of resolution is so extremely low as about 3%.

SUMMARY OF THE INVENTION

After elaborate studies to obtain optically active L- or D-valine hydrochloride efficiently, the inventors of the present invention have found that the improved yield of resolution can be attained by optically resolving the DL-valine hydrochloride in a solvent containing an amine salt, a sulfonic acid, or a carboxylic acid.

The present invention has been accomplished on the basis of the above findings.

Thus, this invention relates to a process for producing optically active valine, characterized by optically resolving DL-valine hydrochloride in a solvent containing an amine salt, a sulfonic acid or a carboxylic acid and isolating an optically active valine after the decomposition of the obtained optically active valine hydrochloride.

DETAILED DESCRIPTION OF THE INVENTION

The process of the present invention can be practiced as follows. DL-valine hydrochloride and an amine salt, sulfonic acid or carboxylic acid, preferably an amine salt, are dissolved in a solvent, if necessary, a small amount of optically active valine hydrochloride is added to solution. DL-valine hydrochloride may be formed by dissolving valine and hydrochloric acid in the resolving solvent. The amine salt may be formed by dissolving amine and acid in resolving solvent.

Subsequently, the solution is cooled or concentrated to supersaturation, and, if necessary with the seeding of crystal of L- or D-valine hydrochloride, the same kind of the optically active isomer is crystallized out; the mixture is subjected to solid/liquid separation and the obtained optically active valine hydrochloride is decomposed to optically active valine, which is collected.

DL-valine hydrochloride may contain partly free DL-valine or, alternatively, free hydrochloric acid.

An amine salt added in the resolving solvent is not particularly limited; for example, lower alkyl amines such as t-butylamine, isobutylamine, n-butylamine, n-hexylamine, isopropylamine, n-propylamine, amylamine, diethylamine, di-n-butylamine, diisopropylamine, triethylamine, tri-n-butylamine, and N,N-diisopropylethylamine, lower alkanolamines such as triethanolamine and N,N-diethanolamine, cycloalkylamines such as cyclohexylamine, cycloalkylmethylamines such as cyclohexane-trismethylamine, aromatic amines such as m-toluidine, and ammonia as basic component, and inorganic acids such as hydrochloric acid and phosphoric acid, organic sulfonic acids such as benzene sulfonic acid and methanesulfonic acid, and organic carboxylic acids such as cyclohexanecarboxylic acid, acetic acid and n-capric acid as acid component may be mentioned, among which, preferable salt is derived from isobutylamine, diethylamine, di-n-butylamine, m-toluidine, diisobutylamine, isopropylamine, n-propylamine, triethanolamine, N,N-diisopropylethylamine, N,N-diethanolamine, t-butylamine and ammonia; more preferable, isopropylamine, n-propylamine, amylamine, triethanolamine, N,N-diisopropylethylamine, N,N-diethanolamine, t-butylamine and ammonia; and the salt of t-butylamine with hydrochloric acid or cyclohexanecarboxylic acid is mentioned as the most preferable.

A sulfonic acid which can be mentioned contains 1 a lower alkylsulfonic acid, for example, methanesulfonic acid, 2 a benzene sulfonic acid, for example, benzene sulfonic acid, o-, m- or p-toluenesulfonic acid and o-, m- or p-xylenesulfonic acid, lower alkyl benzenesulfonic acids, o-, m- or p-nitrobenzenesulfonic acid and halogenobenzene sulfonic acids such as o-, m- or p-chlorobenzenesulfonic acid and sulfanilic acid, and 3 a naphthalenesulfonic acid such as α- or β-naphthalenesulfonic acid, among which β-naphthalenesulfonic acid, sulfanilic acid, p-toluenesulfonic acid and benzenesulfonic acid are preferable and particularly p-toluenesulfonic acid and benzenesulfonic acid are more preferable.

A carboxylic acid which can be mentioned contains fatty acids ($C_1$–$C_6$) such as formic acid, acetic acid, propionic acid, butyric acid, isobutyric acid, pivalic acid, valeric acid, n-caproic acid, etc., cycloalkyl carboxylic acids such as cyclohexane carboxylic acid etc., lower alkyl ($C_2$–$C_5$) oxyacids such as α-hydroxypentanoic acid, etc., among which formic acid, butyric acid and cyclohexane carboxylic acid are preferable.

The content of those substances in solvent is 0.1 to 15 w/w % of the supersaturated solution of DL-valine hydrochloride, preferably 0.5 to 10 w/w %, and more preferably 1 to 8 w/w %. The concentration of valine hydrochloride in supersaturated solution may be in wide range from 15 to 70 w/w % in practice, preferably 20 to 60 w/w %.

The solvents used in the present invention are not particularly limited so long as valine hydrochloride can be dissolved between room temperature and boiling point, and the solution formed therefrom is supersaturated by cooling, concentration or addition of other solvent to precipitate valine hydrochloride; water, hydrophilic organic solvents, for example, alcohols such as methanol, ethanol, isopropylalcohol, etc., or aqueous solvent thereof are preferable. In case water is used, optical resolution may be performed by decreasing solubility of valine hydrochloride by means of addition of inorganic salts such as sodium chloride and sodium sulfate, etc. or inorganic acids such as hydrochloric acid. In those aqueous solution the concentration of inorganic salt or acid is 0 to 15 w/w %, preferably 5 to 12 w/v %.

The temperature is maintained between 0° C. and the boiling point of the solvent during dissolution, preferably from 20° C. to the boiling point.

Although the temperature of crystallization is not particularly limited so long as below the boiling point of the solvent used, it is preferable in the range from 10° C. to 60° C. When the optically active valine hydrochloride thus obtained is not optically pure, recrystallization can easily give, if necessary, optically pure active valine hydrochloride.

The isolation of optically active valine from the obtained optically active valine hydrochloride can be performed by a well-known method. For example, the isolation can be readily performed by dissolving or dispersing optically active valine hydrochloride in water or water-miscible organic solvent containing water, neutralizing the solution with an alkali to decompose optically active valine hydrochloride, concentrating the neutralizing solution to precipitate optically active valine and filtering the precipitate, or by passing an aqueous solution of the optically active valine hydrochloride through a column of a strongly acidic ion exchange resin, washing the column with water, eluting the column with ammonia water, concentrating the eluate and filtering the precipitated crystals.

The yields of resolution by the process described in the following Examples and the known process (see C.A. Vol. 59, 11659D) in Reference Example are summarized in Table I.

This table shows that the yield of resolution according to the present invention surpasses the yield by the known process.

NaOH to pH 6.0, the solution was concentrated to 20 ml, then the formed crystal was filtered, washed with water and dried to obtain 4.90 g of L-valine.

$[\alpha]_D^{20} + 28.1°$ (C=8 in 6N HCl)

EXAMPLE 2

76.93 g of DL-valine hydrochloride, 4.05 g of L-valine hydrochloride and 4.0 g of t-butylamine hydrochloride were added to 119.02 g of 10% aqueous solution of common salt, and heated at 45° C. to solution. This solution was cooled to 24° C. at the rate of 1° C. per 10 minutes, and seeded with 0.15 g of L-valine hydrochloride. After 15 minutes from seeding, the precipitated crystal was subjected to solid/liquid separation and dried to obtain 8.33 g of L-valine hydrochloride.

$[\alpha]_D^{20} + 14.35°$ (C=2 in H$_2$O)

The optical purity of this crystal was 92.6%.

This L-valine hydrochloride was dissolved in 30 ml of water, and the solution was passed through a column of strongly acidic ion-exchange resin Dowex HCR [H+], hereafter eluted with 5% ammoniacal water. The

TABLE I

Effects of substance added in resolution of L-valine hydrochloride crystal

| | | Valine hydrochloride | | | | Optical purity (%) E | Pure L-valine HCl salt (g) F[1] | Gain of resolution (g) G[2] | Yield of resolution (%) Y[3] |
|---|---|---|---|---|---|---|---|---|---|
| Example No. | Substances added | Charged DL (g) A | Charged L (g) B | Seed L (g) C | Obtained L (g) D | | | | |
| Reference | — | 74.05 | 3.90 | 0.50 | 6.93 | 81.2 | 5.63 | 1.23 | 3.32 |
| 1 | p-Toluenesulfonic acid.H$_2$O | 80.47 | 4.23 | 0.50 | 10.53 | 76.8 | 8.09 | 3.36 | 8.35 |
| 2 | t-butylamine.HCl | 76.93 | 4.05 | 0.15 | 8.17 | 92.6 | 7.57 | 3.37 | 10.82 |
| 3 | Pivalic acid | 101.76 | 0 | 2.48 | 6.40 | 85.3 | 5.46 | 2.98 | 5.76 |
| 4 | N,N—Diisopropyl-ethylamine.HCl | 76.89 | 4.05 | 0.50 | 8.65 | 85.1 | 7.36 | 2.81 | 9.03 |
| 5 | t-Butylamine.cyclo-hexanecarboxylic acid | 76.40 | 4.02 | 0.50 | 8.69 | 90.8 | 7.89 | 3.37 | 10.97 |

Note:
[1] F = D × E/100
[2] G = F − B − C
[3] Y = 2G/A

EXAMPLE 1

80.47 g of DL-valine hydrochloride, 4.24 g of L-valine hydrochloride and 11.93 g of p-toluenesulfonic acid monohydrate were added to 102.12 g of 10% aqueous solution of common salt, and heated at 50° C. to solution. This solution was cooled to 22.7° C., then seeded with 0.50 g of L-valine hydrochloride at the same temperature. After 3 minutes, the precipitated crystal was subjected to solid/liquid separation, and by drying this crystal, 10.53 g of L-valine hydrochloride was obtained.

$[\alpha]_D^{20} + 11.9°$ (C=2 in H$_2$O)

The optical purity of the obtained crystal was 76.81% according to calculation based on the optical pure L-valine hydrochloride $[\alpha]_D^{20} + 15.5°$ (C=2 in H$_2$O).

This L-valine hydrochloride was dissolved with 16 ml of 6N hydrochloric acid by heating, then cooled to room temperature to obtain 7.12 g of L-valine hydrochloride ($[\alpha]_D^{20} + 15.2°$ (C=2 in H$_2$O)). This crystal was dissolved in 20 ml of water, and after adjusted with 4N eluate was concentrated to 12 ml and the precipitated crystal was filtered, washed with water and dried to obtain 5.30 g of L-valine.

$[\alpha]_D^{20} + 28.0°$ (C=8 in 6N HCl)

EXAMPLE 3

101.76 g of DL-valine hydrochloride and 4.00 g of pivalic acid were dissolved in 98.24 g of an aqueous solution containing 4% iso-propylalcohol at 45° C., and cooled to 25° C. This solution was seeded with 2.84 g of L-valine hydrochloride, and after 3 minutes the precipitated crystal was subjected to solid/liquid separation, followed by drying to obtain 6.54 g of L-valine hydrochloride.

$[\alpha]_D^{20} + 13.22°$ (C=2 in H$_2$O)

The optical purity of this crystal was 85.32%. The L-valine hydrochloride was treated in the same manner as in Example 1 to obtain L-valine.

EXAMPLE 4

76.89 g of DL-valine hydrochloride, 4.05 g of L-valine hydrochloride and 4.0 g of N,N-diisopropylethylamine hydrochloride were added to 10% aqueous solution of common salt and dissolved at 50° C., and this solution was cooled at 24° C. and seeded with 0.5 g of L-valine hydrochloride. After 5 minutes from seeding, the precipitated crystal was subjected to solid/liquid separation, and dried to obtain 8.65 g of L-valine hydrochloride.

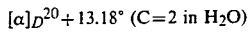
$[\alpha]_D^{20} + 13.18°$ (C=2 in H$_2$O)

The optical purity of this crystal was 85.05%. The L-valine hydrochloride was treated in the same manner as in Example 1 to obtain L-valine.

EXAMPLE 5

76.40 g of DL-valine hydrochloride, 4.02 g of L-valine hydrochloride and 4.00 g of t-butylamine cyclohexane carboxylate were dissolved in 119.58 g of 10% aqueous solution of common salt, and this solution was cooled at 20.5° C., then seeded with 0.50 g of L-valine hydrochloride. After 10 minutes, the precipitated crystal was subjected to solid/liquid separation. The formed crystal was dried to obtain 8.69 g of L-valine hydrochloride.

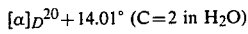
$[\alpha]_D^{20} + 14.01°$ (C=2 in H$_2$O)

The optical purity of this crystal was 90.8%. The L-valine hydrochloride was treated in the same manner as in Example 1 to obtain L-valine.

EXAMPLE 6

58.67 g of DL-valine, 3.05 g of L-valine, 58.69 g of 35% hydrochloric acid, 11.90 g of common salt and 2.67 g of t-butylamine were added to 80.92 g of water, and heated at 45° C. to solution, thereafter the solution was treated in the same manner as in Example 1 to obtain 5.9 g of L-valine.

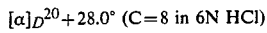
$[\alpha]_D^{20} + 28.0°$ (C=8 in 6N HCl)

REFERENCE EXAMPLE 74.05 g of DL-valine hydrochloride and 3.90 g of L-valine hydrochloride were added to 114.70 g of 10% aqueous solution of common salt, and heated at 50° C. to solution. Thereafter, this solution was cooled to 24° C., and at the same temperature was seeded with 0.50 g of L-valine hydrochloride. After 3 minutes, the precipitated crystal was subjected to solid/liquid separation. This crystal was dried to obtain 6.93 g of L-valine hydrochloride.

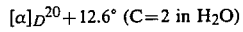
$[\alpha]_D^{20} + 12.6°$ (C=2 in H$_2$O)

The oplical purity of this crystal was 81.23%.

What is claimed is:

1. A process for producing optically active valine, which comprises optically resolving DL-valine hydrochloride in a solvent selected from the group consisting of water and hydrophilic organic solvents and containing substances selected from the group consisting of an amine salt, a sulfonic acid and a carboxylic acid and isolating optically active valine after the decomposition of the obtained optically active valine hydrochloride, wherein the concentration of said amine salt, sulfonic acid or carboxylic acid in a solvent is 0.1 to 15 w/w%, based on the supersaturated solution of DL-valine hydrochloride.

2. A process according to claim 1, wherein said amine salt is salt of lower alkyl amine, lower alkanolamine, cycloalkyl amine, cycloalkyl methyl amine, aromatic amine or ammonia with hydrochloric acid, organic sulfonic acid or carboxylic acid.

3. A process according to claim 1, wherein said amine salt is salt of t-butylamine, isopropylamine, n-propylamine, amylamine, triethanolamine, N,N-diisopropyl ethylamine, N,N-diethanolamine or ammonia with hydrochloric acid or cyclohexane carboxylic acid.

4. A process according to claim 1, wherein said sulfonic acid is a lower alkyl sulfonic acid, a benzene sulfonic acid or a naphthalene sulfonic acid.

5. A process according to claim 1, wherein said carboxylic acid is selected from the group consisting of fatty acid C$_1$-C$_6$, cycloalkyl carboxylic acid, lower alkyl (C$_1$-C$_5$) oxyacid.

6. A process according to claim 1, where said solvent is water, alcohol or aqueous alcohol.

7. A process according to claim 1, wherein said solvent is 0 to 15 w/v % aqueous solution of hydrochloric acid or common salt.

8. A process according to claim 1, wherein the concentration of DL-valine hydrochloride in a solvent is 15 to 70 w/w % based on the supersaturated solution of DL-valine hydrochloride.

9. A process for producing optically active valine, which comprises dissolving DL-valine, t-butylamine and hydrochloric acid in 5 to 12 w/v % aqueous solution of common salt to form DL-valine hydrochloride and t-butylamine hydrochloride, supersaturating the solution to obtain supersaturated solution, wherein the concentration of DL-valine hydrochloride and t-butylamine hydrochloride are 20 to 60 w/w % and 1 to 8 w/w % respectively, precipitating optically active valine hydrochloride from said supersaturated solution, and then isolating optically active valine after decomposition of the obtained optically active valine hydrochloride.

* * * * *